(12) United States Patent
Shimmick et al.

(10) Patent No.: US 6,497,701 B2
(45) Date of Patent: *Dec. 24, 2002

(54) METHOD AND SYSTEM FOR ABLATING SURFACES WITH PARTIALLY OVERLAPPING CRATERS HAVING CONSISTENT CURVATURE

(75) Inventors: John Karl Shimmick, Belmont, CA (US); George Caudle, San Jose, CA (US); Kingman Yee, San Jose, CA (US); Stephen J. Koons, Sunnyvale, CA (US)

(73) Assignee: VISX, Incorporated, Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,810

(22) Filed: Apr. 30, 1999

(65) Prior Publication Data

US 2002/0151878 A1 Oct. 17, 2002

(51) Int. Cl.[7] ................................. A61B 18/18
(52) U.S. Cl. .................. 606/5; 606/4; 606/10; 606/17; 128/898; 351/206; 351/237; 351/246
(58) Field of Search .................. 606/4–6, 11–13, 606/16–19; 364/474.08; 351/200–215, 220, 221, 237, 246; 128/898

(56) References Cited

U.S. PATENT DOCUMENTS

| | | |
|---|---|---|
| 2,480,737 A | 8/1949 | Jayle |
| 3,074,407 A | 1/1963 | Moon |
| 3,476,112 A | 11/1969 | Elstein |
| 3,697,889 A | 10/1972 | Dewey, Jr. |
| 3,743,965 A | 7/1973 | Offner |
| 3,848,104 A | 11/1974 | Locke |

(List continued on next page.)

FOREIGN PATENT DOCUMENTS

| | | |
|---|---|---|
| CA | 1243732 | 10/1984 |
| EP | 0 151869 A1 | 8/1985 |
| EP | 0296982 A1 | 6/1988 |

(List continued on next page.)

OTHER PUBLICATIONS

Eimerl et al. "Optical, mechanical, and thermal properties of barium borate" *J. Appl. Phys.* (1987) 62(5):1968–1983.

(List continued on next page.)

*Primary Examiner*—Linda C. M. Dvorak
*Assistant Examiner*—A. Farah
(74) *Attorney, Agent, or Firm*—Townsend and Townsend and Crew LLP

(57) ABSTRACT

A technique for laser sculpting a predetermined shape on an exposed corneal surface by ablating a sequence of consistently curved craters with individual pulses of a laser beam. An initial laser beam energy pattern is shaped by a laser beam shaping element to make a consistently curved laser beam energy pattern. The consistently curved laser beam ablates a consistently curved crater in the surface with a single pulse of the laser beam. A computer controls the position of the laser beam and scans the laser beam over the surface to sculpt the predetermined shape in an ablation zone on the exposed surface. A sequence of partially overlapping craters is distributed over the ablation zone. In some embodiments diffractive optics are used as a beam shaping element. In additional embodiments, the consistently curved crater is a uniformly curved spherical crater.

47 Claims, 10 Drawing Sheets

U.S. PATENT DOCUMENTS

| | | | |
|---|---|---|---|
| 3,938,058 A | 2/1976 | Yamamoto | |
| 3,982,541 A | 9/1976 | L'Esperance, Jr. | |
| 3,983,507 A | 9/1976 | Tang et al. | |
| 4,169,663 A | 10/1979 | Murr | |
| 4,180,751 A | 12/1979 | Ammann | |
| 4,349,907 A | 9/1982 | Campillo et al. | |
| 4,386,428 A | 5/1983 | Baer | |
| 4,423,728 A | 1/1984 | Lieberman | |
| 4,461,294 A | 7/1984 | Baron | |
| 4,477,159 A | 10/1984 | Mizuno et al. | |
| 4,520,816 A | 6/1985 | Schachar et al. | |
| 4,526,171 A | 7/1985 | Schachar | |
| 4,538,608 A * | 9/1985 | L'Esperance, Jr. | 606/5 |
| 4,546,773 A | 10/1985 | Kremer et al. | |
| 4,573,467 A | 3/1986 | Rich et al. | |
| 4,580,559 A | 4/1986 | L'Esperance, Jr. | |
| 4,598,714 A | 7/1986 | Kremer et al. | |
| 4,619,259 A | 10/1986 | Graybill et al. | |
| 4,633,866 A | 1/1987 | Peyman et al. | |
| 4,653,495 A | 3/1987 | Nanaumi | |
| 4,662,370 A | 5/1987 | Hoffman et al. | |
| 4,665,913 A | 5/1987 | L'Esperance, Jr. | |
| 4,669,466 A | 6/1987 | L'Esperance, Jr. | |
| 4,688,570 A | 8/1987 | Kramer et al. | |
| 4,718,418 A | 1/1988 | L'Esperance, Jr. | |
| 4,720,189 A | 1/1988 | Heyman et al. | |
| 4,721,379 A | 1/1988 | L'Esperance, Jr. | |
| 4,729,372 A | 3/1988 | L'Esperance, Jr. | |
| 4,729,373 A | 3/1988 | Peyman | |
| 4,732,148 A | 3/1988 | L'Esperance, Jr. | |
| 4,764,930 A | 8/1988 | Bille et al. | |
| 4,770,172 A | 9/1988 | L'Esperance | |
| 4,773,414 A | 9/1988 | L'Esperance, Jr. | |
| 4,784,135 A | 11/1988 | Blum et al. | |
| 4,798,204 A | 1/1989 | L'Esperance, Jr. | |
| 4,807,623 A | 2/1989 | Lieberman | |
| 4,838,266 A | 6/1989 | Koziol et al. | |
| 4,838,679 A | 6/1989 | Bille | |
| 4,840,175 A | 6/1989 | Peyman | |
| 4,848,340 A | 7/1989 | Bille et al. | |
| 4,856,513 A | 8/1989 | Muller | |
| 4,862,886 A | 9/1989 | Clarke et al. | |
| 4,896,015 A | 1/1990 | Taboada et al. | |
| 4,901,718 A * | 2/1990 | Bille et al. | 606/4 |
| 4,903,695 A | 2/1990 | Warner et al. | |
| 4,907,586 A | 3/1990 | Bille et al. | |
| 4,911,711 A * | 3/1990 | Telfair et al. | 606/5 |
| 4,925,523 A | 5/1990 | Braren et al. | |
| 4,941,093 A * | 7/1990 | Marshall et al. | 606/5 |
| 4,968,130 A | 11/1990 | Hideshima et al. | |
| 4,975,918 A | 12/1990 | Morton | |
| 4,993,826 A | 2/1991 | Yoder | |
| 4,994,058 A | 2/1991 | Raven et al. | |
| 5,019,074 A | 5/1991 | Muller | |
| 5,052,004 A | 9/1991 | Gratze et al. | |
| 5,063,942 A | 11/1991 | Kilmer et al. | |
| 5,065,046 A | 11/1991 | Guyer | |
| 5,074,859 A | 12/1991 | Koziol | |
| 5,102,409 A | 4/1992 | Balgorod | |
| 5,108,388 A | 4/1992 | Trokel | |
| 5,108,412 A | 4/1992 | Krumeich et al. | |
| 5,133,726 A | 7/1992 | Ruiz et al. | |
| 5,144,630 A * | 9/1992 | Lin | 372/22 |
| 5,152,759 A * | 10/1992 | Parel et al. | 606/5 |
| 5,163,934 A | 11/1992 | Munnerlyn | |
| 5,163,936 A | 11/1992 | Black et al. | |
| 5,182,759 A | 1/1993 | Anthon et al. | |
| 5,188,631 A | 2/1993 | L'Esperance, Jr. | |
| 5,196,006 A | 3/1993 | Klopotek et al. | |
| 5,207,668 A | 5/1993 | L'Esperance, Jr. | |
| 5,217,452 A | 6/1993 | O'Donnell | |
| 5,219,343 A | 6/1993 | L'Esperance, Jr. | |
| 5,219,344 A | 6/1993 | Yoder, Jr. | |
| 5,222,960 A | 6/1993 | Poley | |
| 5,226,903 A | 7/1993 | Mizuno | |
| 5,250,062 A | 10/1993 | Hanna | |
| 5,257,988 A | 11/1993 | L'Esperance, Jr. | |
| 5,263,950 A | 11/1993 | L'Esperance, Jr. | |
| 5,284,477 A * | 2/1994 | Hanna et al. | 606/5 |
| 5,288,292 A | 2/1994 | Giraud et al. | |
| 5,290,301 A | 3/1994 | Lieberman | |
| 5,312,320 A | 5/1994 | L'Esperance, Jr. | |
| 5,324,281 A | 6/1994 | Muller | |
| 5,334,190 A * | 8/1994 | Seiler | 606/5 |
| 5,336,217 A | 8/1994 | Buys et al. | |
| 5,345,534 A | 9/1994 | Najm et al. | |
| 5,349,590 A | 9/1994 | Amirkhanian et al. | |
| 5,350,374 A | 9/1994 | Smith | |
| 5,353,262 A | 10/1994 | Yakymyshyn et al. | |
| 5,360,424 A | 11/1994 | Klopotek | |
| 5,363,388 A | 11/1994 | Shi et al. | |
| 5,364,388 A | 11/1994 | Koziol | |
| 5,370,641 A | 12/1994 | O'Donnell, Jr. | |
| 5,395,356 A | 3/1995 | King et al. | |
| 5,395,362 A | 3/1995 | Sacharoff et al. | |
| 5,405,355 A | 4/1995 | Peyman et al. | |
| 5,411,501 A | 5/1995 | Klopotek | |
| 5,423,801 A | 6/1995 | Marshall et al. | |
| 5,425,727 A | 6/1995 | Koziol | |
| 5,425,729 A | 6/1995 | Ishida et al. | |
| 5,437,658 A | 8/1995 | Muller et al. | |
| 5,441,511 A | 8/1995 | Hanna | |
| 5,442,487 A | 8/1995 | Mizuno | |
| 5,445,633 A | 8/1995 | Nakamura et al. | |
| 5,461,212 A | 10/1995 | Seiler et al. | |
| 5,470,329 A | 11/1995 | Sumiya | |
| 5,474,548 A | 12/1995 | Knopp et al. | |
| 5,480,396 A * | 1/1996 | Simon et al. | 606/4 |
| 5,505,723 A | 4/1996 | Muller | |
| 5,507,741 A | 4/1996 | L'Esperance, Jr. | |
| 5,507,799 A * | 4/1996 | Sumiya | 606/5 |
| 5,520,679 A | 5/1996 | Lin | |
| 5,549,597 A | 8/1996 | Shimmick et al. | |
| 5,556,395 A | 9/1996 | Shimmick et al. | |
| 5,582,752 A | 12/1996 | Zair | |
| 5,599,340 A | 2/1997 | Simon et al. | |
| 5,613,965 A | 3/1997 | Muller | |
| 5,624,436 A | 4/1997 | Nakamura et al. | |
| 5,634,920 A | 6/1997 | Hohla | |
| 5,637,109 A * | 6/1997 | Sumiya | 606/5 |
| 5,642,287 A * | 6/1997 | Sotiropoulos et al. | 364/474.08 |
| 5,646,791 A | 7/1997 | Glockler | |
| 5,651,784 A | 7/1997 | Klopotek | |
| 5,683,379 A | 11/1997 | Hohla | |
| 5,684,562 A | 11/1997 | Fujieda | |
| 5,711,762 A | 1/1998 | Trokel | |
| 5,713,892 A | 2/1998 | Shimmick | |
| 5,722,971 A * | 3/1998 | Peyman | 606/5 |
| 5,735,843 A | 4/1998 | Trokel | |
| 5,782,822 A | 7/1998 | Telfair et al. | |
| 5,807,381 A * | 9/1998 | Lieberman | 606/5 |
| 5,827,264 A * | 10/1998 | Hohla | 606/5 |
| 5,849,006 A | 12/1998 | Frey et al. | |
| 5,865,830 A | 2/1999 | Parel et al. | |
| 5,906,608 A * | 5/1999 | Sumiya et al. | 606/5 |
| 5,984,916 A * | 11/1999 | Lai | 606/11 |
| RE37,504 E | 1/2002 | Lin | |

FOREIGN PATENT DOCUMENTS

| | | |
|---|---|---|
| EP | 0151869 B1 | 1/1990 |
| EP | 0368512 A2 | 5/1990 |

| | | |
|---|---|---|
| EP | 0207648 B1 | 8/1990 |
| EP | 0418890 A3 | 3/1991 |
| EP | 0602756 A1 | 6/1994 |
| WO | PCT/FR87/00139 | 11/1987 |
| WO | PCT/US92/09625 * | 5/1993 ............ A61N/5/02 |
| WO | PCT/US93/00327 | 8/1993 |
| WO | PCT/US94/02007 | 9/1994 |
| WO | PCT/EP95/01287 | 10/1995 |

OTHER PUBLICATIONS

Complete *Reissue File History of U.S. Patent No.* 5,520,679 to Lin (Reissue filed May 27, 1998) Reissued as U.S. Patent No. RE 37,504 on Jan. 8, 2002.

Ren et al, "Corneal Refractive Surgery ..Solid State Laser", Opth. Tech, vol. 1423, pp 129–139, 1991.*

Qiushi Ren, Raymond P. Galitis, Keith P. Thompson, & J.t. Lin, "Ablation of the Cornea and Synthetic Polymers Using a UV (213 nm) Solid State Laser", IEEE Journal of Quatum Electronics, Dec. 1990, pp. 2284–2288.

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

J.T. Lin, J.L. Montgomery, "Temperature—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperatures", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, Third—Harmonic Generation of an Alexandrite Laser in $\beta$–$BaB_2O_4$, Applied Physics Letters, May 1989, pp. 1206–1208.

Conference on Lasers and Electro–Optics, Optical Society of America, Apr. 1989, p. 390.

Barraquer, "Lamellar Keratoplasty (special techniques)" Annals of Ophthalmology, Jun. 1972, pp. 437–469.

Burnett, "Company Denies Delay in Approval for Laser", Orlando Sentinel, Feb. 1993, pp. 12–13.

Burnett, "Medical Technology", Orlando Sentinel, Feb. 1993, pp. 1–5.

Gailitis et al., "Solid State Ultraviolet Laser (213 nm) Ablation of the Cornea and Synthetic Collagen Lenticules", Lasers in Surgery and Medicine, Dec. 1991, pp. 556–562.

Gartry et al., "Excimer Laser Photorefractive Keratectomy", Ophthalmology, Aug. 1992, pp.. 1210–1219.

Gilbert, "Corneal Topography: In Search of the Excimer Islands", Eye Care Technolgy, Oct. 1993, pp. 23–28.

L'Esperance, "New Laser Systems, Their Potential Clinical Usefulness, and Investigative Laser Procedures", Ophthalmic Lasers, 1989, pp. 995–1045.

Lin et al, "Corneal Topography Following Excimer Photorefractive Kerectomy for Myopia", Journal of Cataract Refractive Surgery, 1993, pp. 149–154.

Lin et al, "A Multiwavelength Solid State Laser for Ophthalmic Applications", Ophthalmic Technolgies, Jun. 1992, pp. 266–275.

Marguerite B. McDonald et al, "Central Photorefractive Keratectomy for Myopia", Ophthalmology, Sep. 1991, pp. 1327–1337.

Marshall et al, "Long–term Healing of the Central Cornea after Photorefractive Keratectomy Using an Excimer Laser", Oct. 1998, pp. 1411–1421.

Marshall et al, "Photoablative Reprofiling of the Cornea Using an Excimer Laser: Photorefractive Keratectomy", Lasers in Ophthalmology, Jan. 1986, pp. 21–48.

McDonald et al., "Central Photorefractive Keratectomy for Myopia", Arch Ophthalmology, Jun. 1990, pp. 799–808.

Palikaris et al, "Excimer Laser in Situ Keratomileusis and Photorefractive Keratectomy for Correction of High Myopia", Journal of Refractive and Corneal Surgery, Sep. 1994, pp. 498–510.

Ren et al, "Corneal Refractive Surgery Using an Ultra–Violet (213 nm) Solid State Laser" Ophthalmic Technologies, Jun. 1991, pp. 129–139.

Rozakis, "Refractive Lamellar Keratoplasty" History of Keratomileusis, 1994, Chapt. 1–13.

Seiler et al, "Excimer Laser (193nm) Myopic Keratomileusis in Sighted and Blind Human Eyes" Refractive and Corneal Laser Surgery, Jun. 1990, pp. 165–173.

Serdarevic, "Corneal Laser Surgery", Ophthalmic Lasers, 1989, pp. 919–970.

Steinert et al, "Laser Corneal Surgery", Laser Research Laboratory, 1998, pp. 151–154.

Thompson et al, "Philosophy and Technique for Excimer Laser Phototheraputic Keratectomy", Refractive and Corneal Surgery, Apr. 1993, pp. 81–85.

Trokel et al Excimer Laser Surgery of the Cornea', American Journal of Ophthalmology, Dec. 1983, pp. 710–715.

Trockel et al, "Evolution of Excimer Laser Corneal Surgery", Jul. 1989, pp. 373–381.

Van Mielaert et al, "On the Safety of 193–Nanometer Excimer Laser Refractive Corneal Surgery" Refractive and Corneal Surgery, Jun. 1992, pp. 235–239.

Wilson et al, "Changes in Corneal Topography after Excimer Laser Photorefractive Keratectomy for Myopia", Ophthalmology, Sep. 1991, pp. 1338–1347.

LaserSight Press Release of Nov. 16, 1992.

"Summit Refutes LaserSight's Assertions", Press Release by Summit Technology, Waltham, Massachusetts, Nov. 17, 1992.

LaserSight Press Release of Nov. 18, 1992.

"LaserSight Denies Device Patent Infringement—Debuts Auto–PRK at ASCRS Convention", Press Release by LaserSight Technologies, Inc, Mar. 31, 1995.

L'Esperance, Jr., Francis A., "Ophthalmic Lasers," vol. II, Third Edition, Chapter 24: Corneal Lase Surgery, The C.V. Mosby Company, St Louis (1989).

* cited by examiner

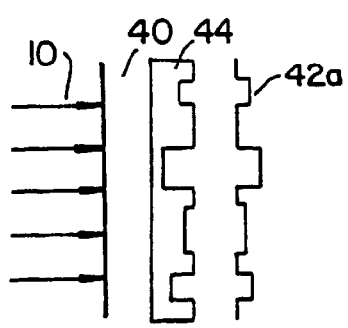
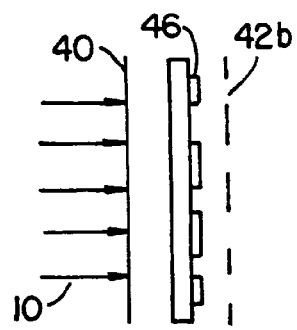
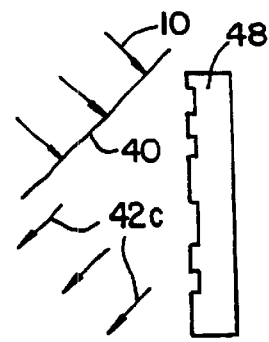
FIG. 4.  FIG. 5.  FIG. 6.
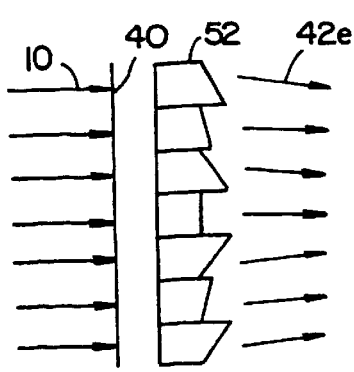
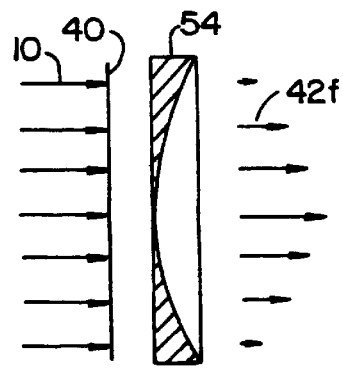
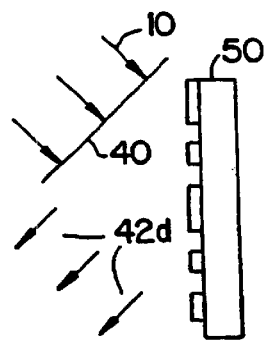
FIG. 8.  FIG. 9.  FIG. 7.
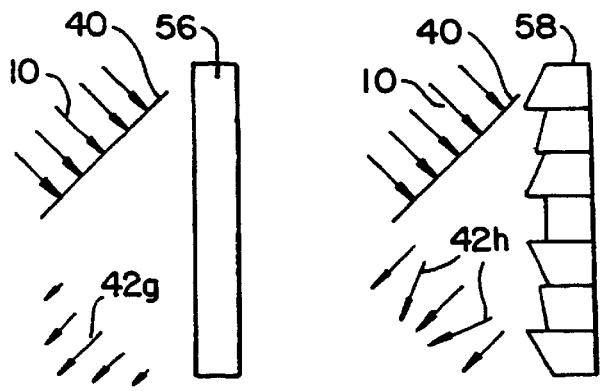
FIG. 10.  FIG. 11.

METHOD AND SYSTEM FOR ABLATING SURFACES WITH PARTIALLY OVERLAPPING CRATERS HAVING CONSISTENT CURVATURE

BACKGROUND OF THE INVENTION

1. Field of the Invention

The present invention relates generally to medical systems and methods. More particularly, the present invention relates to the use of laser delivery systems for generating successive patterns of light energy for ablating corneal tissue.

Photorefractive keratectomy (PRK) and phototherapeutic keratectomy (PTK) employ optical beam delivery systems for directing laser energy to a patient's eye. The laser selectively ablate corneal tissue to reform the shape of the cornea and improve vision. Existing commercial systems employ pulsed lasers to ablate tissue from the eye. With these laser systems, each laser beam pulse ablates a crater in the tissue of the eye, and subsequent laser beam pulses ablate additional craters. A desired predetermined shape is sculpted in the corneal tissue by adjusting at least one of the position, size and shape of the craters made by the individual pulses.

The cornea includes an outer epithelial layer, a Bowman's layer beneath the epithelial layer and a stromal layer beneath Bowman's layer. At least a portion of the ablated predetermined shape is ablated in a layer beneath the epithelial layer. In order to achieve ablation of a layer beneath the epithelium, a layer of tissue is removed and a surface of the underlying tissue is exposed. This exposed surface of the cornea is ablated with the laser beam to sculpt a predetermined shape in the exposed surface. After the photorefractive keratectomy procedure, the epithelium rapidly regrows over the shaped area, producing a new anterior surface of the cornea. Alternatively, the epithelium is not removed but is partially severed and moved to the side for surgery and returned to its original position after the PRK.

The output beam from the lasers used in laser eye surgery systems is typically irregular and often requires treatment with special optics to create a more desirable beam. For example, the beams from the lasers are often spatially and temporally integrated in order to form a beam having uniform characteristics. In particular, the beams are integrated in order to display a flat or uniform intensity profile over a circular target region, often referred to as a "top hat" profile. Alternatively, the laser beam may be cropped to select a portion of the beam having uniform characteristics, or the beam may be focused onto the eye to form a Gaussian energy profile distribution.

Once a desired beam shape is achieved, a laser beam may be used in different ways in order to effect corneal ablation. In a first type of system, the beam has a variable cross-sectional size. The maximum size generally corresponds to the total treatment area on the cornea. The beam size is manipulated using an iris or other exposure control mechanism, and the desired corneal reshaping can be achieved by properly controlling the exposure. Unfortunately, employing a laser beam having a size equal to the treatment area (typically on the order of 5.0 mm to 10.0 mm) requires the use of large, high pulse energy excimer lasers. Not only are such large lasers expensive, they also occupy a relatively large area, requiring significant space to house them. Another disadvantage of laser systems employing large uniform beams is that the shape ablated with a uniform beam is not necessarily uniform. For large diameter beams, work in connection with the present invention has suggested that the ablated shape may depend upon a variety of factors, including the hydration of the cornea. Unfortunately, hydration may vary across the surface of the cornea, and can be difficult to measure.

As an alternative to large variable size laser beam systems, laser scanning systems are also employed for corneal ablation. Scanning systems often employ a much smaller beam, minimizing energy required from the laser. The smaller lasers are also more economic and require less space. The use of a small beam width, however, complicates certain aspects of the treatment protocols. In particular, the laser pulses will partially overlap as the beam is scanned over the exposed surface of the cornea. This partial overlap of the beams causes the ablated craters to partially overlap and the ablated surface to become rough. Roughening of the ablated surface is undesirable because it can cause a cornea to scar and delay the recovery of visual acuity. Another disadvantage of this scanning approach has been the relatively small amount of tissue removed with each pulse of the laser beam. Because of the small amount of tissue removed, the laser must be used at very high pulse rates to keep the total treatment time within acceptable limits. These high pulse rates can cause tissue heating, resulting in scarring and loss of visual acuity.

Another approach has been to scan a variable size laser beam. This approach moves the laser beam over the treatment area while changing the size of the beam, and has been shown to be both effective and highly flexible. Unfortunately, this approach often involves fairly complex and expensive mechanical mechanisms and electrical circuitry. Additionally, overlap of the pulses often occurs during scanning, and this overlap causes the ablation to become rougher.

A disadvantage of the above scanning approaches is that a crater ablated by an individual pulse of the laser beam does not have a consistent curvature. This lack of consistent curvature in the ablated crater causes the exposed surface to become rougher as the tissue is sculpted to a desired shape. For example, scanning laser systems that have a laser beam energy profile with a uniform energy distribution will typically ablate individual craters having a steep wall and a flat central region. The peripheral region of the crater that includes the steep side wall has a very different curvature than the flat central region. Scanning laser systems with Gaussian or pseudo-gaussian laser beam energy profiles ablate craters having a cone-shaped edge with a rounded central region. The peripheral region of the crater (including the cone-shaped edge) again has a different curvature than the central region (including the rounded portion of the crater). The inconsistent curvature of a cornea ablated by these known scanning systems may limit the accuracy and benefit of resculpting procedures.

The use of large laser beams with a tailored energy density has also been suggested. First, it may be difficult to ablate complex shapes with this approach. Also, this approach requires the use of expensive lasers to produce large beams. As mentioned earlier, with large diameter ablations the ablated shape will depend upon the hydration of the cornea, and tissue hydration is difficult to measure. Consequently, this technique will produce variability in the ablated shape including central underablation that undesirably degrades visual acuity.

For the above reasons, it would be desirable to provide improved methods and systems for ablating corneal tissue.

It would further be desirable to provide improved techniques for the scanning of light beams over corneal tissue in order to selectively ablate the tissue to treat vision disorders. In particular, it would be desirable to utilize small beam geometries with low pulse energy requirements while achieving a smooth ablation. Also, it would be desirable to more accurately ablate the surface to a desired shape with less dependence upon tissue hydration. Moreover, it would be desirable to simplify the control schemes and systems for scanning light beams for corneal treatment. At least some of these objectives will be met by the invention described hereinafter.

2. Description of the Background Art

Large beam variable width systems for performing photorefractive keratectomy (PRK) and phototherapeutic keratectomy are described in a number of patents including U.S. Pat. Nos. 4,973,330, 5,163,934, 4,732,148 and 4,729,372. A temporal and spatial beam integrator for a PRK/PTK laser system is described in U.S. Pat. No. 5,646,791.

Scanning systems for performing photorefractive keratectomy (PRK) and phototherapeutic keratectomy (PTK) are described in a number of patents, including U.S. Pat. No. 4,718,418 and 4,665,913. A laser surgical system employing a diffractive optical element adapted to an individual patient is described in U.S. Pat. No. 5,571,107.

Scanning variable width laser beam systems are described in issued U.S. Pat. No. 5,683,379 and a co-pending patent application entitled "Method and System for Laser Treatment of Refractive Errors Using Offset Imaging," U.S. patent application Ser. No. 08/058,599, filed on May 7, 1993, the full disclosures of which are herein incorporated by reference.

Laser ablation techniques using large width laser beams with a graded energy density are described in U.S. Pat. Nos. 5,219,343, 5,312,320, 5,207,668, 5,188,631 and 4,838,266, the full disclosures of which are herein incorporated by reference.

Use of a diffractive optical element is described in a co-pending applications entitled "Laser Delivery System and Method with Diffractive Optic Beam Integration," U.S. patent application Ser. No. 09/015,841, filed on Jan. 29, 1998; "Method and System for Scanning Non-Overlapping Patterns of Laser Energy with Diffractive Optics," U.S. patent application Ser. No. 09/116,648, filed on Jul. 16, 1998, the full disclosures of which are herein incorporated by reference.

The full disclosures of each of the above-cited U.S. patents and applications are incorporated herein by reference.

SUMMARY OF THE INVENTION

The present invention provides improved methods, systems, and other apparatus for performing laser ablation. The present invention significantly improves the uniformity of treatment by scanning beams having energy distribution profile shapes that ablate craters with a consistent curvature. Preferably, the beams are scanned so as to cover the entire ablation zone with partially overlapping craters that have consistent curvature. The present invention provides a number of specific improvements over prior corneal ablation methods and systems. The technique provides for sculpting a surface with partially overlapping consistently curved craters. In some embodiments, the technique provides for sculpting a surface with partially overlapping uniformly curved craters. Typically, a laser sculpting to achieve a desired optical result will ablate the surface with a uniform or gradually varying change in curvature. For example, spherical corrections of near sightedness produce a uniform concave change in curvature, and the correction of hyperopia produces a uniform convex change in curvature. Advantageously, laser sculpting to correct an astigmatic curvature of the eye can exhibit a gradual change in curvature over the ablated surface. Similarly, other refractive errors and aberrations (such as mixed astigmatism, presbyopia and wavefront aberrations) may be treated with the technique without having to resort to incremental, stepped approximations of the desired smooth curvature.

In a first aspect, the invention provides methods for sculpting a region on a surface. The methods generally include directing pulsed beams toward the region and ablating craters with the beam pulses. The craters will often have a consistent curvature, the craters optionally being rounded and axissymmetric in shape. The beam is scanned over the region to effect a predetermined change in shape by partially overlapping the craters.

A dimension across the ablation craters is often about 5 to 80% of the dimension across the treatment region. In some embodiments, the curvature of the craters is substantially uniform and spherical, and the craters are of a substantially uniform size. The pulsed energy beam is preferably a laser beam. In some embodiments, the technique includes shaping the laser beam with a beam shaping element. In other embodiments, the technique includes diffracting the laser beam with a laser beam diffracting element.

In another aspect, the invention provides a laser system for sculpting an ablated region on a surface of a tissue to a predetermined shape. The laser system includes a pulsed laser for making a pulsed beam of an ablative laser energy, and a beam energy shaping element for changing a laser beam energy pattern of the pulsed beam to a shaped beam. The shaped beam includes a consistently curved laser beam energy pattern with a region of the consistently curved pattern above the threshold of ablation of the tissue. The system also includes a scanning element for moving the shaped beam over the region to sculpt the region with a plurality of partially overlapping pulses of the ablative energy.

The shaped beam may include a boundary enclosing the curved pattern and an intensity of the beam around the boundary may be a proportion of the threshold of ablation, the proportion being in a range of 100 to 150%. In some embodiments, the consistently curved laser beam pattern is a substantially spherical laser beam energy pattern.

BRIEF DESCRIPTION OF THE DRAWINGS

FIG. 4 illustrates a diffracting element for shaping the laser beam by changing the phase of the laser beam passing through the element.

FIG. 5 illustrates a diffracting element for shaping the laser beam by changing the amplitude of the laser beam passing through the element.

FIG. 6 illustrates a diffracting element for shaping the laser beam by changing the phase of the laser beam reflecting from the element.

FIG. 7 illustrates a diffracting element for shaping the laser beam by changing the amplitude of the laser beam reflecting from the element.

FIG. 8 illustrates an array of prisms for shaping the laser beam by redistributing the energy of the laser beam.

FIG. 9 illustrates an intensity varying transmitting element for varying the intensity of the laser beam transmitted through the element.

FIG. 10 illustrates an intensity varying reflective element for varying the intensity of the laser beam reflected from the element.

FIG. 11 illustrates an angle varying reflective element for shaping the laser beam by varying the angle of reflection of the laser beam.

DESCRIPTION OF THE SPECIFIC EMBODIMENTS

Figure 1:
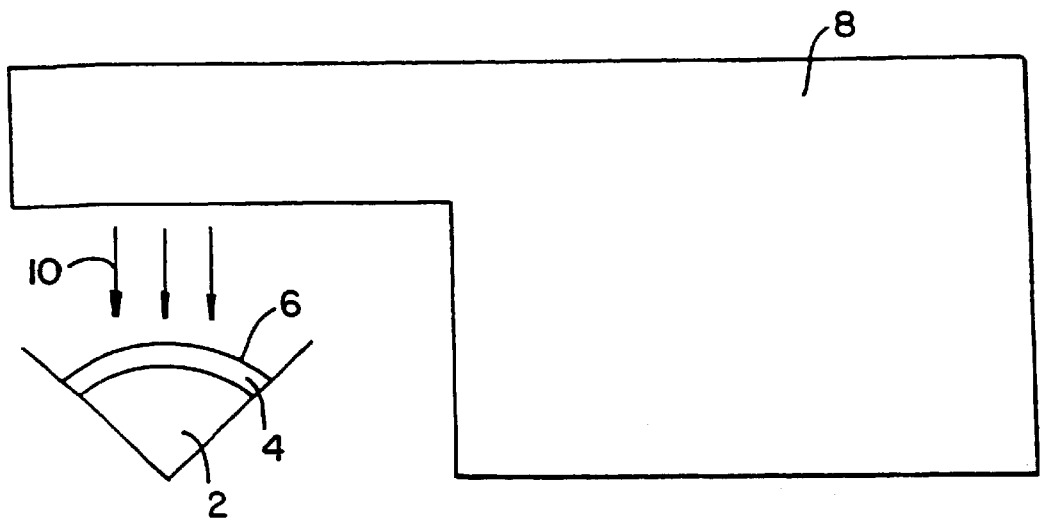
FIG. 1 illustrates a laser system for sculpting an eye to a desired shape with a laser beam.

The present invention is generally directed to structures, systems, and methods for treating a human eye. In particular, the techniques of the present invention are well suited for sculpting an exposed surface of a human eye to a desired shape. The techniques of the present invention generally improve the accuracy and smoothness to which a desired shape may be sculpted on an eye. The invention is particularly useful for performing corneal ablation in PRK and PTK procedures, but will also be useful for removing an epithelial layer prior to stromal ablation in such procedures. For convenience, the following discussion will be directed at stromal ablation, but the teachings are also useful for removing epithelial tissue.

As used herein, scanning means that a light beam moves between successive, discrete locations on the corneal surface. Those locations are then exposed to a predetermined amount or dosage of the light energy. Usually, the laser system will be operated in a pulsed manner, and the exposure at any particular location will result from a number of pulses which occur over a very short time period. The total area of the cornea to be treated, referred to hereinafter as the "ablation zone," is eventually treated as the ablative light beam is scanned over the zone.

Mathematically, the shape of a crater can be defined as the change in surface profile topography caused by a pulse of the laser beam. The curvature along a surface can be expressed as the change in slope along the surface. For a rotationally symmetric crater such as a spherical crater, the curvature of the crater can be approximated by the second derivative of a crater surface contour line displaced radially outward from a center of the crater. The second derivative and corresponding curvature of a region of a crater can be positive, negative or zero. Positive curvature for a region of a crater is a curvature that provides positive optical power over a small region of a crater ablated in a flat surface. Positive optical power will cause a small bundle of parallel light rays passing through a small region of the crater to converge toward a common point. Negative optical power will cause a small bundle of parallel light rays passing through a small region of the crater to diverge. A small region of a crater is a region corresponding to about one tenth of the surface area of the crater. Negative curvature for a crater is a curvature that provides negative optical power over a crater ablated in a flat surface. A consistently curved crater is a crater that has a negative optical power over most of the ablated crater surface. The magnitude of the negative optical power may vary over the crater surface. A crater having uniform curvature will have a negative curvature with a substantially constant magnitude. A spherical crater has a uniform curvature, and for most ablated surfaces a parabolic crater will approximate a spherical crater and have a uniform curvature. A crater with a substantially positive curvature will also have regions with a negative curvature and not have a consistent curvature.

Partial overlap of the craters is overlap wherein a region of each of the overlapping craters is shared with another region of another overlapping crater and each of the overlapping craters also has a region that is outside the shared region. Similarly, partial overlap of the laser beam is overlap wherein a region of each of the overlapping laser beams is shared with another region of another overlapping laser beam, and each of the overlapping laser beams also has a region that is outside the shared region. A crater is the shape ablated with a single pulse of the laser beam. Alternatively, a crater may be the shape ablated with a single position of the laser beam. With this scanning technique, the entire ablation zone can be treated with the desired dosage of ablative energy.

Turning now to the figures, FIG. 1 illustrates a laser system for reshaping a surface of an eye. An eye 2 has a cornea 4. The cornea 4 is located in the anterior portion of the eye 2. The cornea 2 has an exposed surface 6. The exposed surface 6 of the cornea 4 is shaped with an ablative laser beam 10. A laser system 8 makes the ablative laser beam 10. The laser system 8 is a scanning laser system.

Figure 2:
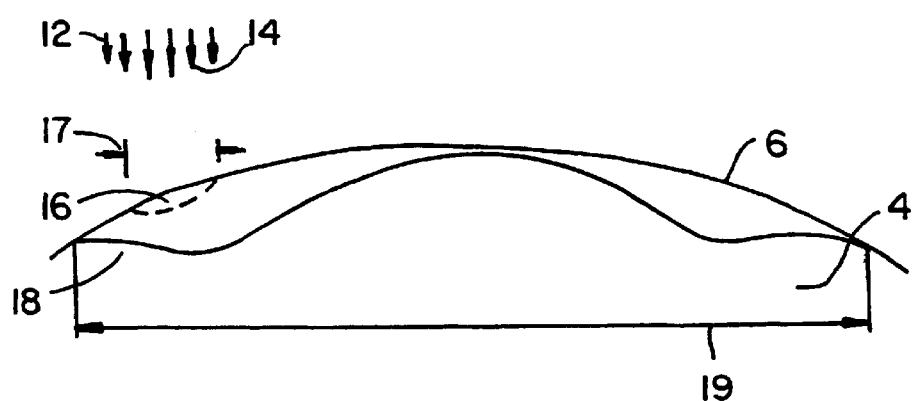
FIG. 2 illustrates an improved technique of the invention for scanning a laser beam over an eye.

A technique of the invention is illustrated in FIG. 2. In this figure, a consistently curved pulsed laser beam 12 ablates the exposed surface 6 of a cornea 4. An individual pulse of the consistently curved pulsed laser beam 12 has a region with consistently curved laser beam energy pattern 14. An individual pulse of the consistently curved pulsed laser beam 12 forms a consistently curved crater 16 in the exposed surface 6. A predetermined shape is sculpted in the ablated region 18 by distributing a plurality of consistently curved craters over the ablated region 18. Scanning a sequence of successive pulses of the consistently curved pulsed laser beam 12 over the ablated region 18 forms the ablated region 18 with the distributed consistently curved craters.

The consistently curved crater 16 has a dimension across the crater 17. The ablated region 18 has a dimension across the ablated region 19. A dimension across the crater 17 is significantly smaller than a dimension across the ablated region 19, the crater typically being in a range from about 5 to about 80% of the size of the treatment region. A dimension across the consistently curved crater 16 will typically range from about 0.5 to 4 mm, and a dimension across the ablated region 19 will typically range from 5 to 10 mm.

Figure 2A:
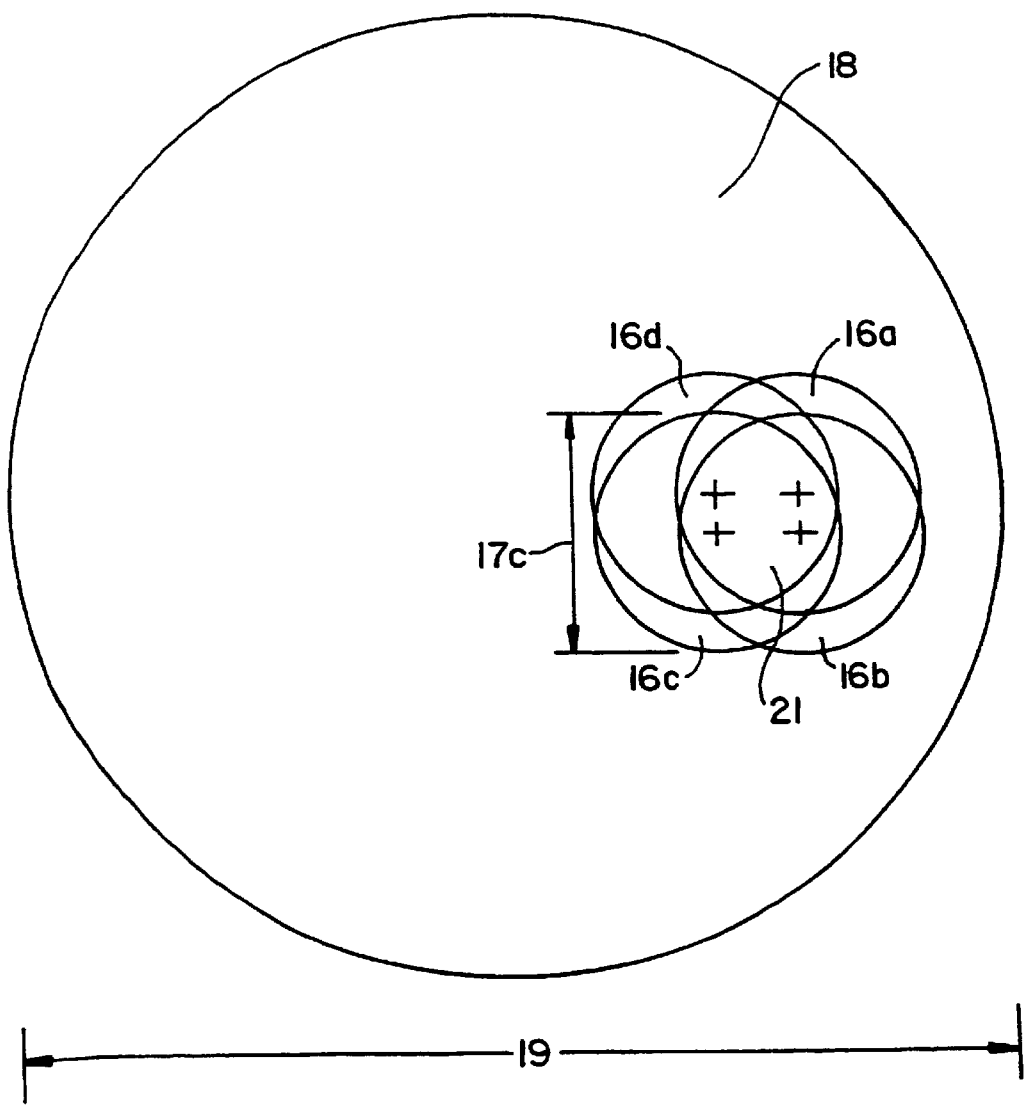
FIG. 2a illustrates a technique of the invention for overlapping consistently curved craters.

A relative positioning of a plurality of consistently curved craters (16a, 16b, 16c and 16d) within an ablated region 18 is illustrated in FIG. 2A. A dimension 17c across a crater 16c is again smaller than a dimension across the ablated region 18. During the laser sculpting, the consistently curved craters (16a, 16b, 16c and 16d) are positioned to partially overlap. The craters are displaced relative to each other, and a partially overlapping area 21 of the consistently curved craters forms within the ablated region 19. The crater dimensions 17 are uniform among the craters 16a, 16b, 16c and 16d. Alternatively, a dimension 17 across a crater may vary among the craters 16a, 16b, 16c and 16d.

Figure 3:
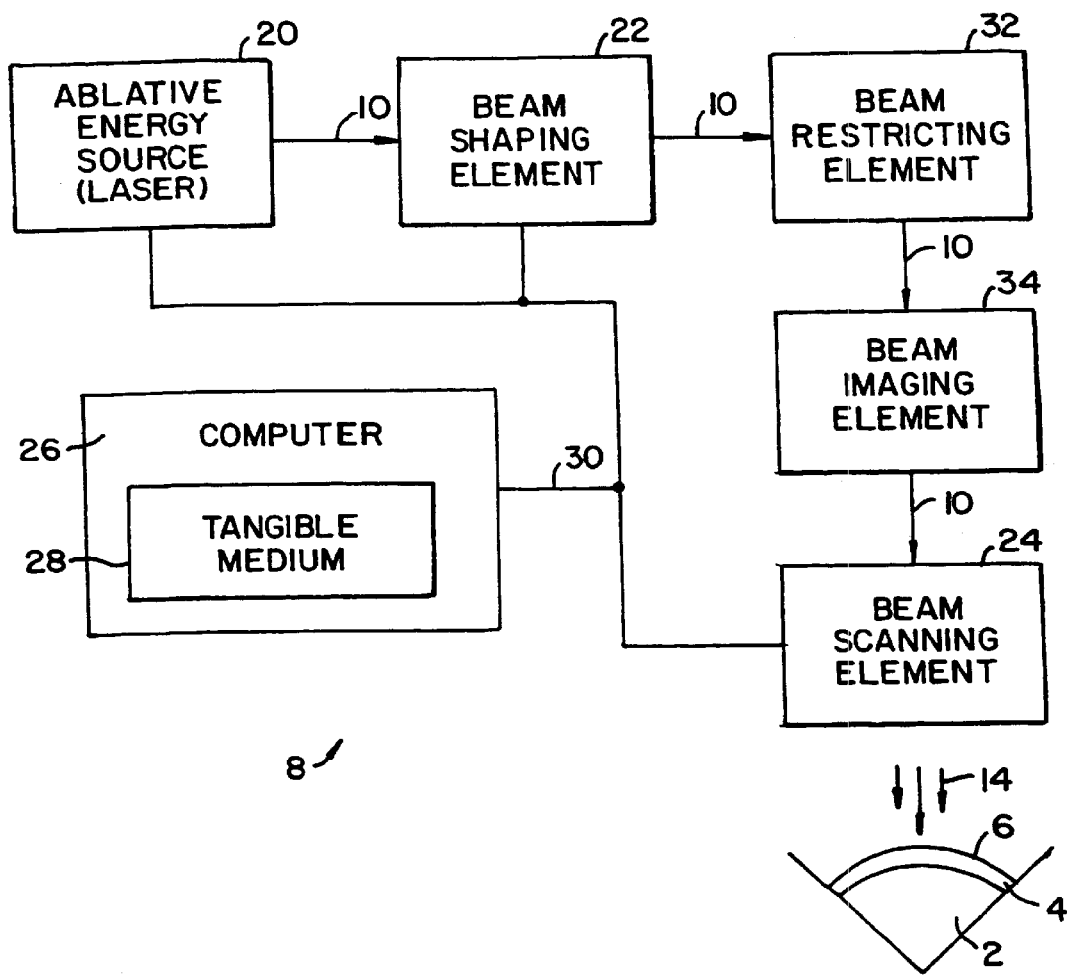
FIG. 3 schematically illustrates a laser system incorporating the improved techniques of the invention.

A schematic diagram generally illustrating the functional elements of the invention is shown in FIG. 3. An ablative energy source 20 is preferably a 193 nm excimer laser, but could be any suitable pulsed laser source emitting electromagnetic radiation that is strongly absorbed by the cornea. For example, the pulsed laser source may emit energy in the far ultraviolet region of the electromagnetic spectrum, or alternatively may emit infrared radiation that is strongly absorbed by the cornea. Suitable far ultraviolet wavelengths range from about 150 to 250 mn, and are more preferably in the range of about 190 to 230 mn. Suitable infrared wavelengths range from about 2 to 10 um, and are more preferably in range of about 2.5 to 3.5 um. Techniques for making lasers emitting continuous wave and pulsed electromagnetic radiation with wavelengths in the above ranges are well known in the art. Suitable lasers include, but are not limited to, excimer lasers such as argon-fluoride excimer lasers (producing laser energy having a wavelength of about 193 nm), and solid state lasers, such as frequency multiplied solid state lasers. Exemplary solid state lasers might be flash-lamp and diode pumped solid state lasers, including UV solid state lasers(approximately 193–215 nm), such as those disclosed in U.S. Pat. Nos. 5,144,630, 5,742,626, Borsuztky et al., "Tunable UV Radiation at Short Wavelengths (188–240 mn) Generated by Sum Frequency Mixing in Lithium Borate," Appl. Phys. 61:529–532 (1995) and the like.

The ablative energy source 20 makes a laser beam 10. A laser beam shaping element 22 is positioned in the path of laser beam 10. The laser beam shaping element 22 shapes an energy distribution across the laser beam 10 to consistently curved laser beam energy pattern 14 near the exposed surface 6. The laser beam shaping element 22 may be optionally rotated between pulses of the laser beam to average the energy profile. A laser beam scanning element 24 scans the consistently curved beam 14 over the ablated region.

A computer 26 includes a tangible medium 28. A signal connection 30 allows the computer 26 to communicate with the ablative energy source 20, the beam shaping element 22 and beam scanning element 24. The computer 26 controls the pulsing of the ablative energy source 20. The computer 26 controls the position of the consistently curved laser beam 12 on the exposed surface 6 of the cornea 4 by articulating the scanning element 24. A coordinate reference from the computer 26 adjusts the scanning element 24 to position the laser beam to a predetermined position on the cornea. The signal connection 30 may be an electronic or fiber optic or any suitable signal connection.

The invention optionally includes a beam restricting element 32 for restricting the size of the laser beam. The restricting element 32 includes an aperture formed of a non-transmitting material that blocks the laser beam. The aperture selectively transmits a portion of the laser beam through the non-transmitting material.

The invention may further optionally include a laser beam imaging element 34. The laser beam imaging element 34 forms an image of the restricted laser beam that is transmitted through the aperture. The image of the restricted beam will form near the exposed surface 6 of the cornea 4. In some embodiments of the invention, the functional elements may be combined. For example, the beam imaging element 34 may be combined with the beam scanning element 24. Other items that may optionally be included with the invention (such as an operating microscope and eye tracker) have been omitted from FIG. 3 to avoid prolixity, as they are well described in the patent literature and/or familiar to those of skill in the art.

FIGS. 4 through 13 illustrate various techniques which may be used to shape laser beams to a desired cross sectional laser beam energy pattern. One approach to shape a laser beam is to diffract the laser beam to a desired laser beam shape by changing an amplitude or a phase of a laser beam with a diffracting element. Diffractive beam shaping techniques are illustrated in FIGS. 4–7. Diffractive beam shaping techniques are described in more detail in U.S. Pat. Nos. 5,610,733, 5,571,107 and a co-pending application entitled LASER DELIVERY SYSTEM AND METHOD WITH DIFFRACTIVE OPTIC BEAM INTEGRATION, U.S. patent application Ser. No. 09/015,841, filed on Jan. 29, 1998, the full disclosures of which are herein incorporated in their entirety. Suppliers capable of designing and manufacturing suitable diffractive optics include the Rochester Photonics Corporation of Rochester, N.Y.; the Digital Optics Corporation of Charlotte N.C.; and MEMS Optical Inc. of Huntsville, Ala. A suitable diffractive optic can be designed to reshape a laser beam energy profile distribution from an initial energy profile distribution to a desired energy profile distribution. Parameters used to design a diffractive optic include the desired reshaped laser beam energy profile distribution and the incident laser beam wavelength, divergence, cross sectional area and energy profile distribution.

A first approach for manipulating the energy distribution so as to ablate a uniformly curved crater with each pulse of a laser beam is illustrated in FIG. 4. This approach varies a phase of an incident light beam by transmitting the beam through the diffractive beam shaping element. An incident wave front 40 of the light beam 10 impinges upon a phase modulating transmitting element 44. The phase modulating transmitting element 44 changes the incident wave front 40 to changed beam 42a having a changed phase. The changed beam has a varying phase that causes the beam to diffract. The diffraction of the beam forms the shaped laser beam having the desired laser beam energy pattern.

An alternative to changing the phase of the beam transmitted through the diffracting element is to change the intensity of the beam passing through the diffracting element as illustrated in FIG. 5. An incident wave front 40 of the laser beam 10 passes through an amplitude modulating transmitting element 46. The changed laser beam 42b has a changed intensity that causes the laser beam to diffract. The diffraction of the changed beam 42b forms the shaped beam having the desired laser beam energy pattern.

An alternate technique for shaping a laser beam by diffraction is to use reflecting diffractive optics as illustrated in FIGS. 6 and 7. A phase modulating reflecting element is illustrated in FIG. 6. An incident wave front 40 of the laser beam 10 reflects off a surface of a phase modulating reflecting element 48. The changed laser beam 42c reflects from a surface of the phase modulating reflecting element 48. The changed beam has a changed phase that causes the beam to diffract. The diffraction of the beam forms the shaped beam having the desired laser beam energy pattern. A related amplitude modulating reflecting element is illustrated in FIG. 7. An incident wave front 40 of the laser beam 10 reflects off a surface of an intensity modulating reflecting element 50. The changed laser beam 42d reflects from a surface of the intensity modulating reflecting element 50. The changed beam has a changed amplitude that causes the beam to diffract. The diffraction of the beam forms the shaped beam having the desired laser beam energy pattern. In general, it should be understood that some portion of the incident beam may be lost due to absorption, unintended reflection, or other inefficiencies with many of these techniques.

Figure 12:
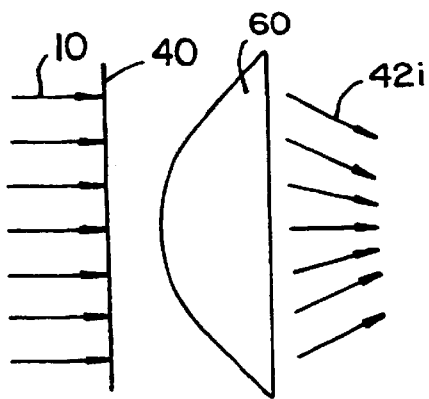
FIG. 12 illustrates an aspheric lens for shaping the laser beam.
Figure 13:
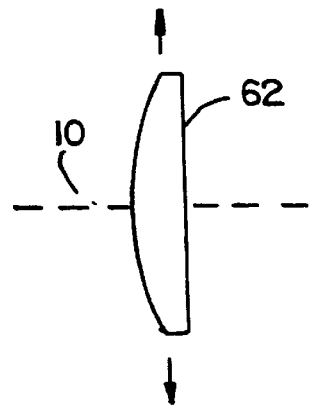
FIG. 13 illustrates a lens used in a beam scanning element.

Another technique for shaping a laser beam is to bend light rays of a beam so as to reshape the laser beam energy pattern. The rays of a beam may be bent so as to shape the beam with either transmitting refractive optics or reflective optics. With either approach, light rays of the beam interact with an angle varying surface of the element that causes the light rays to be bent to change the energy distribution of the laser beam. The energy of the laser beam is redistributed to form a laser beam with a desired laser beam energy pattern. The exact shape of an angle varying element will depend upon the nature of the incident laser beam and the desired laser beam energy pattern. Angle varying transmitting refractive elements suitable for shaping laser beams include lenses, prisms and aspheric optics as illustrated in FIGS. 8, 12 and 13. Angle varying reflecting optics suitable for shaping laser beams include mirrors such as flat mirrors, parabolic mirrors, spherical mirrors, cylindrical mirrors and segmented mirrors. An example of a suitable mirror is the segmented mirror illustrated in FIG. 11.

With the transmitting refractive element shown in FIG. 8, an array of prisms 52 interact with the wave front 40 of laser a laser beam 10 to create a changed beam 42e. The changed beam 42e will overlap portions of the beam to change the beam energy pattern to a consistently curved beam energy pattern. U.S. Pat. No. 5,646,791 describes the use of a prism array to create a uniform energy profile laser beam energy pattern, the entire disclosure of which is herein incorporated by reference. An aspheric optic used as an angle varying transmitting refractive element is illustrated in FIG. 12. A wave front 40 of an incident laser beam 10 is transmitted through the aspheric lens 60 to create a changed laser beam 42i. The changed laser beam 42i will redistribute the energy of the laser beam to create a consistently curved laser beam energy pattern. A spherical lens 62 is illustrated in FIG. 13. A spherical lens 62 may be used to change a laser beam energy pattern to a consistently curved laser beam energy pattern.

With the angle varying reflecting optic shown in FIG. 11, a wave front 40 of the incident laser beam 10 is changed by an angle varying reflecting surface to produce changed laser beam 42h. The changed beam 42h will overlap portions of the beam to change the beam energy pattern to a consistently curved beam energy pattern.

A further technique for shaping a laser beam energy pattern to a consistently curved energy pattern is to gradually grade or variably absorb the intensity of the laser beam with the beam shaping element. For example, the intensity grading transmitting element shown in FIG. 9 variably transmits the laser beam to produce a consistently curved laser beam. An incident wave front 40 of a laser beam 10 is partially absorbed by the intensity grading transmitting optic 54 to make the shaped laser beam 42f. A partially absorbing material in the intensity grading transmitting optic 54 will absorb a portion of the laser beam energy and transmit a remaining portion of the laser beam energy. A technique for shaping transmitted laser beams is described in U.S. Pat. No. 4,838,266, the entire disclosure of which is herein incorporated by reference. A related intensity grading reflecting element will change the shape of a laser beam, as illustrated in FIG. 10. The intensity grading reflecting optic 56 variably reflects the laser beam 10. An incident wave front 40 of a laser beam 10 is variably reflected by a surface of the intensity grading reflecting optic 54 to make the shaped laser beam 42f. A technique for grading reflected laser beams is described in U.S. Pat. No. 5,219,243, the entire disclosure of which is herein incorporated by reference.

If desired, the above laser beam shaping elements may be combined to produce a laser beam shaping element with improved characteristics. For example, a diffractive optic as illustrated in FIG. 4 may be combined with a lens as illustrated in FIG. 13. A co-pending application describes the use of a lens with a diffractive optic to shape a laser beam, and is entitled "Laser Delivery System and Method with Diffractive Optic Beam Integration," U.S. patent application Ser. No. 09/015,841, filed on Jan. 29, 1998, the full disclosure of which is incorporated herein by reference. A similar combined diffractive optic/lens approach may provide the consistently curved laser beam described herein. Alternatively, a phase modulating transmitting technique may be combined with an amplitude modulating transmitting technique. The combined diffractive technique will change both the amplitude and phase of an incident wave front as the wave front interacts with the diffractive optical element. A technique for changing both an amplitude and a phase of an incident wave front is described in U. S. Pat. No. 5,571,107, the entire disclosure of which is herein incorporated by reference.

Figure 14:
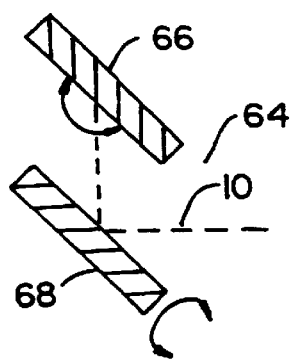
FIG. 14 illustrates an XY mirror assembly used in a beam scanning element.
Figure 15:
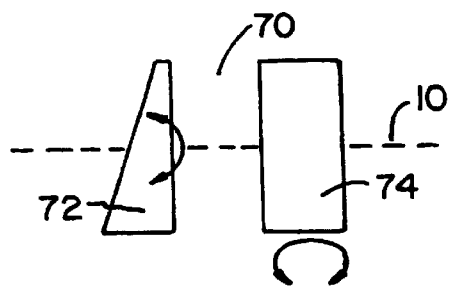
FIG. 15 illustrates an XY prism assembly used in a beam scanning element.
Figure 16:
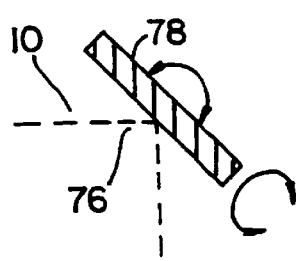
FIG. 16 illustrates a gimbaled mirror used in a beam scanning element.
Figure 17:
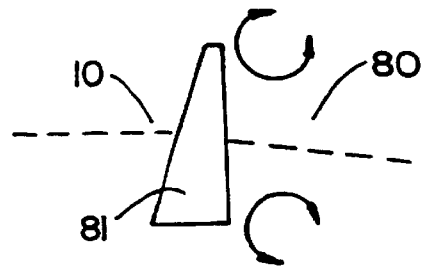
FIG. 17 illustrates a gimbaled prism used in a beam scanning element.

Laser beam scanning elements suitable for use as laser beam scanning element 24 are illustrated in FIGS. 13–17. The laser beam scanning element deflects the laser beam by moving an optical element. Optical elements used in scanning element 24 include lenses prisms and mirrors. A lens 62 may be used to scan a laser beam 10 as illustrated in FIG. 13. Moving lens 62 transverse to a laser beam 10 will deflect the beam to a desired position on the eye. U.S. patent application Ser. No. 08/058,599, filed on May 7, 1993, entitled "Method and System for Laser Treatment of Refractive Errors Using Offset Imaging," describes the use of a moving lens to scan a laser beam, the entire disclosure of which is herein incorporated by reference. An XY mirror assembly 64 is illustrated in FIG. 14. A first axis mirror 66 moves to deflect the laser beam 10 along a first axis. A second axis mirror 68 moves to deflect the laser beam 10 along a second axis. An XY prism assembly is illustrated in FIG. 15. A first axis prism 72 moves to deflect the laser beam 10 along a first axis. A second axis prism 74 moves to deflect the laser beam 10 along a second axis. A gimbaled mirror assembly 76 is illustrated in FIG. 16. A gimbaled mirror 78 is rotated along two axes of rotation to deflect laser beam 10 to a desired position. A gimbaled prism assembly 80 is illustrated in FIG. 17. A gimbaled prism 81 is rotated along two axes of rotation to deflect laser beam 10 to a desired position.

Figure 18:
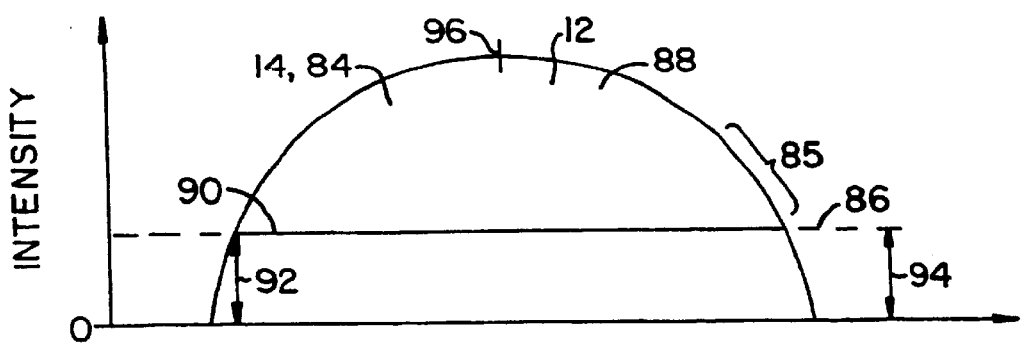
FIG. 18 illustrates a cross sectional intensity profile of a spherical laser beam energy pattern.
Figure 18A:
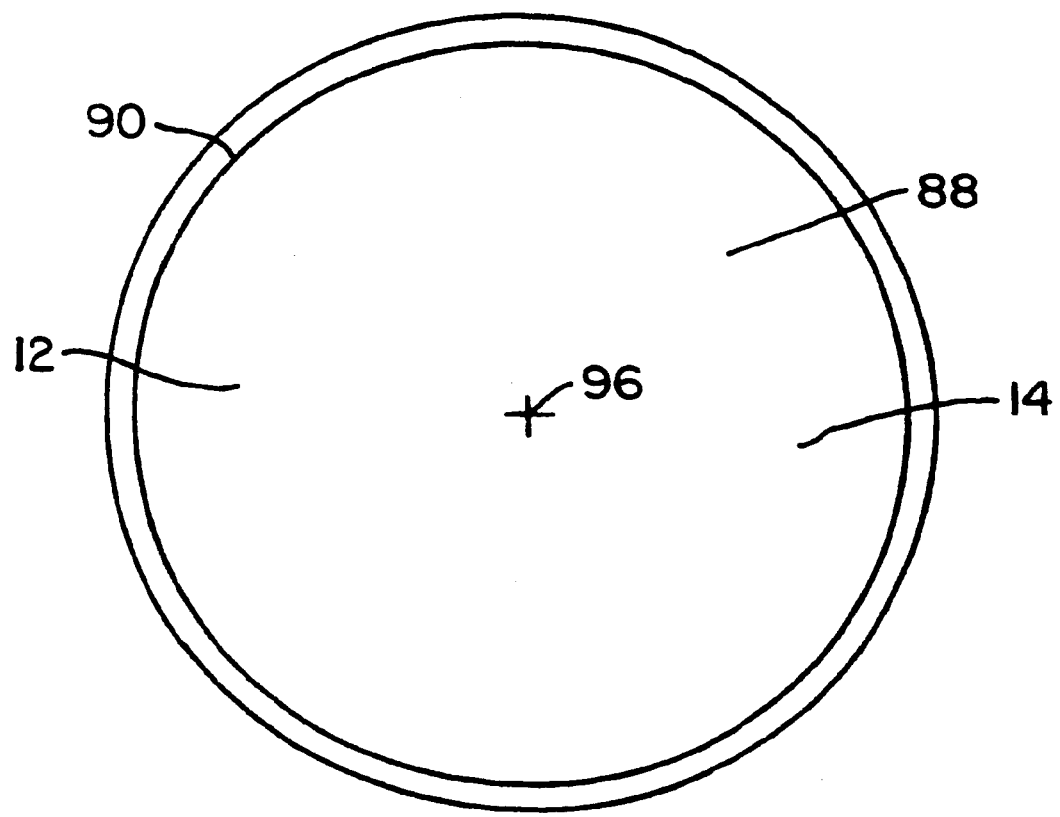
FIG. 18A illustrates a cross sectional view of a spherical laser beam energy pattern.

A consistently curved laser beam energy pattern 14 of a consistently curved pulsed laser beam 12 is illustrated in FIG. 18. The consistently curved laser beam energy pattern 14 is a generally spherical laser beam energy pattern 84. The generally spherical laser beam energy pattern 84 is created with a laser beam shaping element as illustrated above. The generally spherical laser beam energy pattern 84 includes a rounded axis symmetric region 85 adjacent the periphery of the laser beam. The rounded axis symmetric region is above a threshold of ablation 86. The intensity of the consistently curved pulsed laser beam 12 is adjusted so that a region 88 of the consistently curved laser beam energy pattern 14 is above a threshold of ablation 86 of the tissue to be ablated. The above threshold region 88 of the consistently curved laser beam energy pattern 14 is enclosed by a boundary 90. An intensity 92 of the laser beam along the boundary 90 is proportional to a laser beam intensity 94 corresponding to a threshold of ablation 86. In FIG. 18, the proportion of the laser beam intensity 92 along the boundary 90 to the intensity 94 corresponding to a threshold of ablation 86 is 100%. The boundary 90 encloses the above threshold region of the laser beam when the above threshold region has a consistently curved laser beam energy pattern. The boundary 90 will form a boundary around a crater formed in an ablated material. When the above threshold region includes a consistently curved region and a region without a consistent curvature, the boundary 90 will form a boundary around the consistently curved region of the ablated crater. The consistently curved pulsed laser beam 12 has a center 96. A cross sectional view of a consistently curved laser beam 12 viewed down the laser beam path is illustrated in FIG. 18a. The consistently curved laser beam 12 has a center 96. An above threshold region 88 of the consistently curved laser beam energy pattern 14 is enclosed by a boundary 90.

Figure 19:
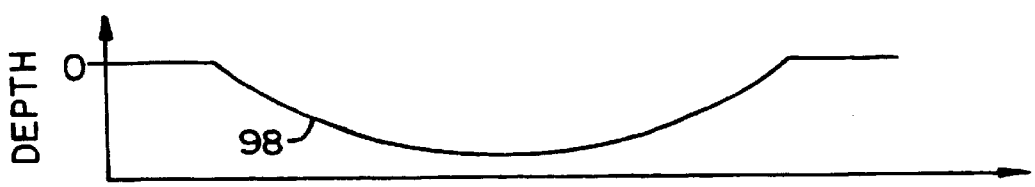
FIG. 19 illustrates a spherical crater ablated in a tissue.

A consistently curved laser beam 14 with a spherical laser beam energy pattern 84 will produce a generally spherical crater 98 in an ablated tissue as illustrated in FIG. 19. The generally spherical crater 98 will be formed in the tissue when the ablation rate of the tissue matches the intensity of the laser beam. Ablation rate refers to the depth of tissue removed with a pulse of a laser beam. The depth of material removed from a region of a crater with a pulse of the beam will generally depend upon the intensity of the laser beam irradiating the region. The shape of an ablated crater can be estimated from a localized intensity of the laser beam irradiating a region of the crater.

Figure 20:
FIG. 20 illustrates an aspheric crater ablated in a tissue.

In some instances, the ablation rate of the tissue will not exactly correspond to the intensity of the laser beam, and the tissue will demonstrate a reduced central ablation (relative to the intensity of a spherical laser beam energy pattern 84). For example, cornea will under ablate centrally relative to the intensity of the central region of the laser beam energy pattern. A spherical laser beam energy pattern 84 will form consistently curved aspheric crater 100 in an ablated cornea as illustrated in FIG. 20. In FIG. 20, the central region of the crater 100 is under ablated relative to a spherical profile. Alternatively, the spherical laser beam energy pattern may make a crater with a flat central region and rounded edges. The crater 100 includes a rounded axis symmetric peripheral region 101. The rounded axis symmetric peripheral region 101 makes smoother ablations when the craters partially overlap.

Figure 21:
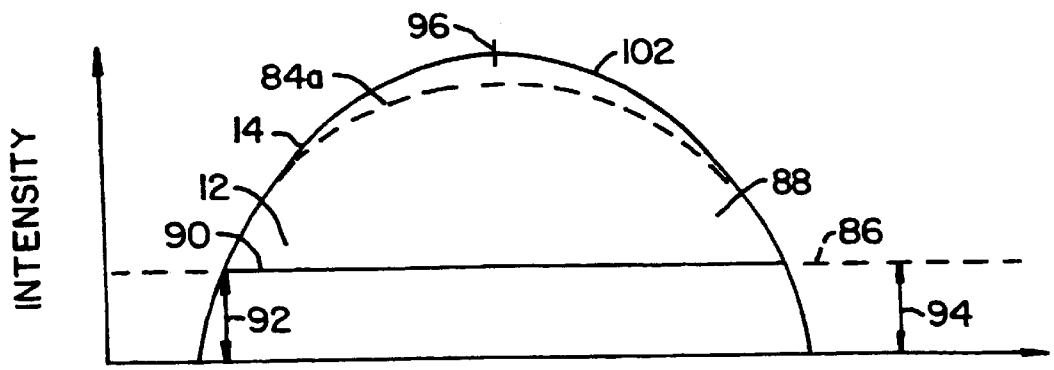
FIG. 21 illustrates a laser beam energy pattern with a hotter than spherical central portion.

For larger laser beam diameters (e.g. about 2 to 5 mm), central under ablation will preferably be corrected by increasing the intensity of the consistently curved laser beam energy pattern 14 to be hotter centrally than a spherical beam as illustrated in FIG. 21. A consistently curved pulsed laser beam 12 has a hotter than spherical central portion 102 as compared to a spherical energy pattern 84a. The hotter than spherical central portion 102 corrects for central under ablation to create a generally spherical crater 98 as illustrated in FIG. 19.

Figure 22:
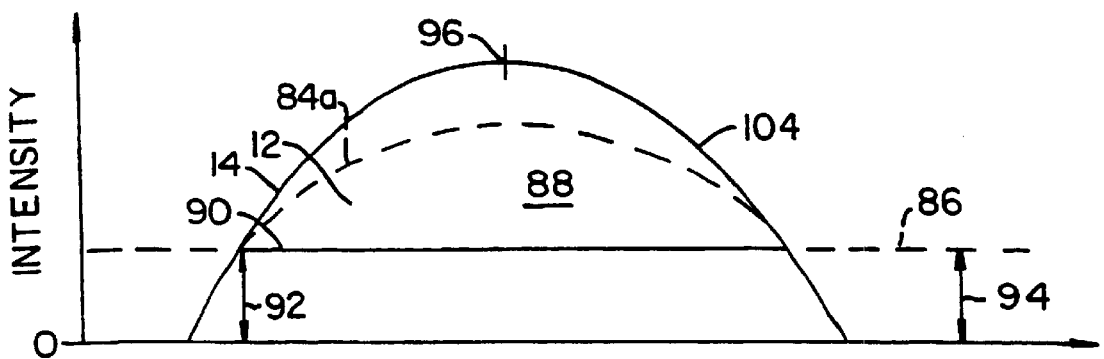
FIG. 22 illustrates an aspheric laser beam energy pattern.

A preferred consistently curved pulsed laser beam energy pattern 14 that corrects for a central under ablation is an aspheric laser beam energy pattern 104 as illustrated in FIG. 22. The aspheric laser beam energy pattern 104 is more intense centrally compared to a spherical laser beam energy pattern 84a. The more intense central region desirably corrects for central under ablation. The intensity of the aspheric laser beam energy pattern 104 gradually tapers to the threshold of ablation peripherally to make a smooth spherical crater 98 as illustrated in FIG. 19.

Figure 23:
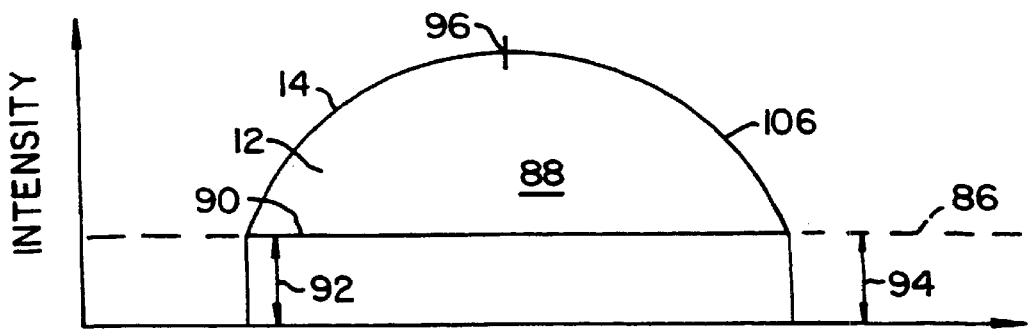
FIG. 23 illustrates a restricted laser beam with a spherical laser beam energy pattern above a threshold of ablation.
Figure 24:
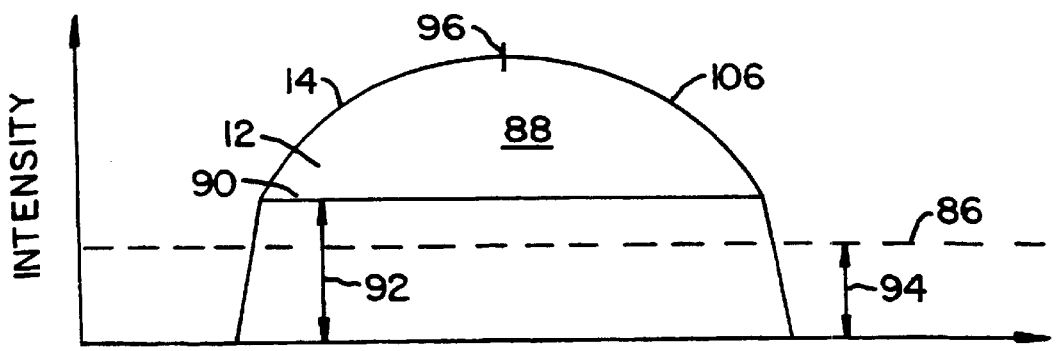
FIG. 24 illustrates a restricted laser beam with a consistently curved laser beam energy pattern above a threshold of ablation, and a boundary around the consistently curved pattern that is also above the threshold of ablation.

During laser ablation, it is undesirable to expose the tissue to a laser beam with an intensity below an intensity 94 threshold of ablation 86. This exposure to laser beam energy below the threshold of ablation does not contribute to the sculpting process, and the sub threshold energy undesirably exposes the tissue to additional radiation. This additional radiation causes damage to the tissue and undesirably heats the tissue. Therefore, the consistently curved beam 12 is preferably restricted to produce a restricted laser beam 106 as illustrated in FIG. 23. The consistently curved laser beam 14 has a center 96. The intensity of the restricted laser beam is adjusted so that a region 88 of the consistently curved laser beam energy pattern 14 is above a threshold of ablation 86 of the tissue to be ablated. The above threshold region 88 of the consistently curved laser beam energy pattern 14 is enclosed by a boundary 90. An intensity 92 of the laser beam along the boundary 90 is proportional to a laser beam intensity 94 corresponding to a threshold of ablation 86. In FIG. 23, the proportion of the laser beam intensity 92 along the boundary 90 to the intensity 94 corresponding to a threshold of ablation 86 is 100%. Alternatively, a proportion of the laser beam intensity 92 along the boundary 90 to the intensity 94 corresponding to a threshold of ablation may be greater than 100% as illustrated in FIG. 24. In FIG. 24, the consistently curved beam 12 is restricted to produce a restricted laser beam 106. The consistently curved laser beam 12 has a center 96. The intensity of the restricted laser beam 106 is adjusted so that a region 88 of the consistently curved laser beam energy pattern 14 is above a threshold of ablation 86 of the tissue to be ablated. The above threshold region 88 of the consistently curved laser beam energy pattern 14 is enclosed by a boundary 90. The proportion of the intensity 92 of the laser beam along the boundary 90 to the intensity 94 of the threshold of ablation 86 is within the range of 100 to 150%. Preferably, the proportion is in the range of 100 to 125% and more preferably in the range of 100 to 110%.

A preferred technique for measuring a laser beam energy pattern is to profile the laser beam with a beam intensity profilometer (BIP) such as a Startech BIP 5100 available from Startech of Danbury, Conn. This BIP is preferably used with Spirocon LBA PC series software available from Spirocon of Logan, Utah. A preferred technique for determining a shape of a crater produced by a laser beam is to profile an ablated cornea as described in U.S. patent application Ser. No. 09/083,773, entitled "Systems and Methods for Imaging Corneal Profiles," filed on May 22, 1999, the entire disclosure of which is herein incorporated by reference. Using the above techniques, a person of ordinary skill in the art can determine the shape of a crater made by an individual pulse of a laser beam for a known laser beam energy profile.

Figure 25:
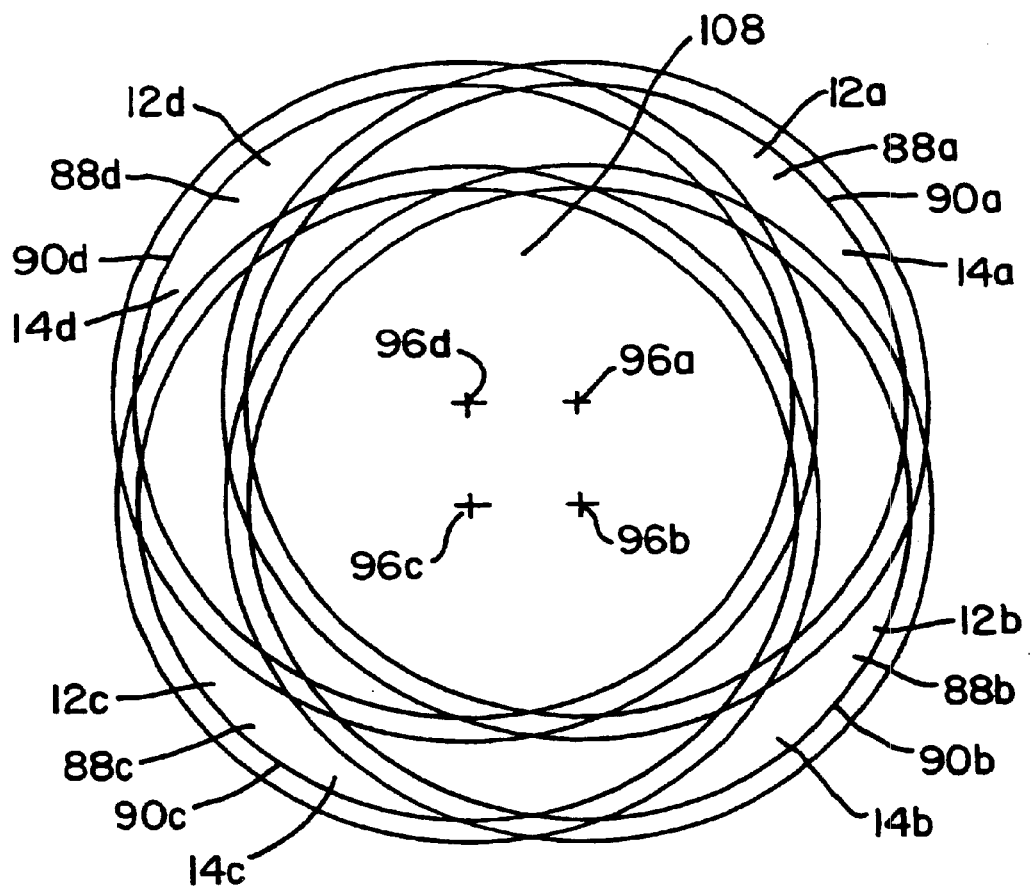
FIG. 25 illustrates an area of overlapping consistently curved laser beam patterns.

The technique of the invention partially overlaps the above threshold region 88 of the consistently curved laser beam pattern 14 from a succession of consistently curved pulsed laser beams as illustrated in FIG. 25. In FIG. 25, four partially overlapping consistently curved pulsed laser beams (12a, 12b, 12c and 12d) are illustrated. The displaced centers (96a, 96b, 96c and 96d) of the four consistently curved pulsed laser beams (12a, 12b, 12c and 12d respectively) illustrate a displacement of the laser beam between pulses of the laser beam. The above threshold regions (88a, 88b, 88c and 88d) of the four consistently curved laser beam patterns (14a, 14b, 14c and 14d) partially overlap. Boundaries 90a, 90b, 90c and 90d enclose the above threshold regions (88a, 88b, 88c and 88d) of the consistently curved beam patterns (14a, 14b, 14c and 14d). A partially overlapping area (108) of the regions (88a, 88b, 88c and 88d) include the centers (96a, 96b, 96c and 96d) of the consistently curved pulsed beams. The displacement of the laser beam is controlled by the coordinate reference in the memory 29 of the computer 26. The coordinate reference in the memory 29 of the computer 26 partially overlaps the consistently curved patterns to form partially overlapping area 108 with sequentially pulsed laser beams. Alternatively, non-sequentially pulsed laser beams may form overlapping area 108. For example several laser beam pulses may occur between a first consistently curved pulsed laser beam 12a, and a partially overlapping subsequent consistently curved pulsed laser beam 12b.

Figure 26:
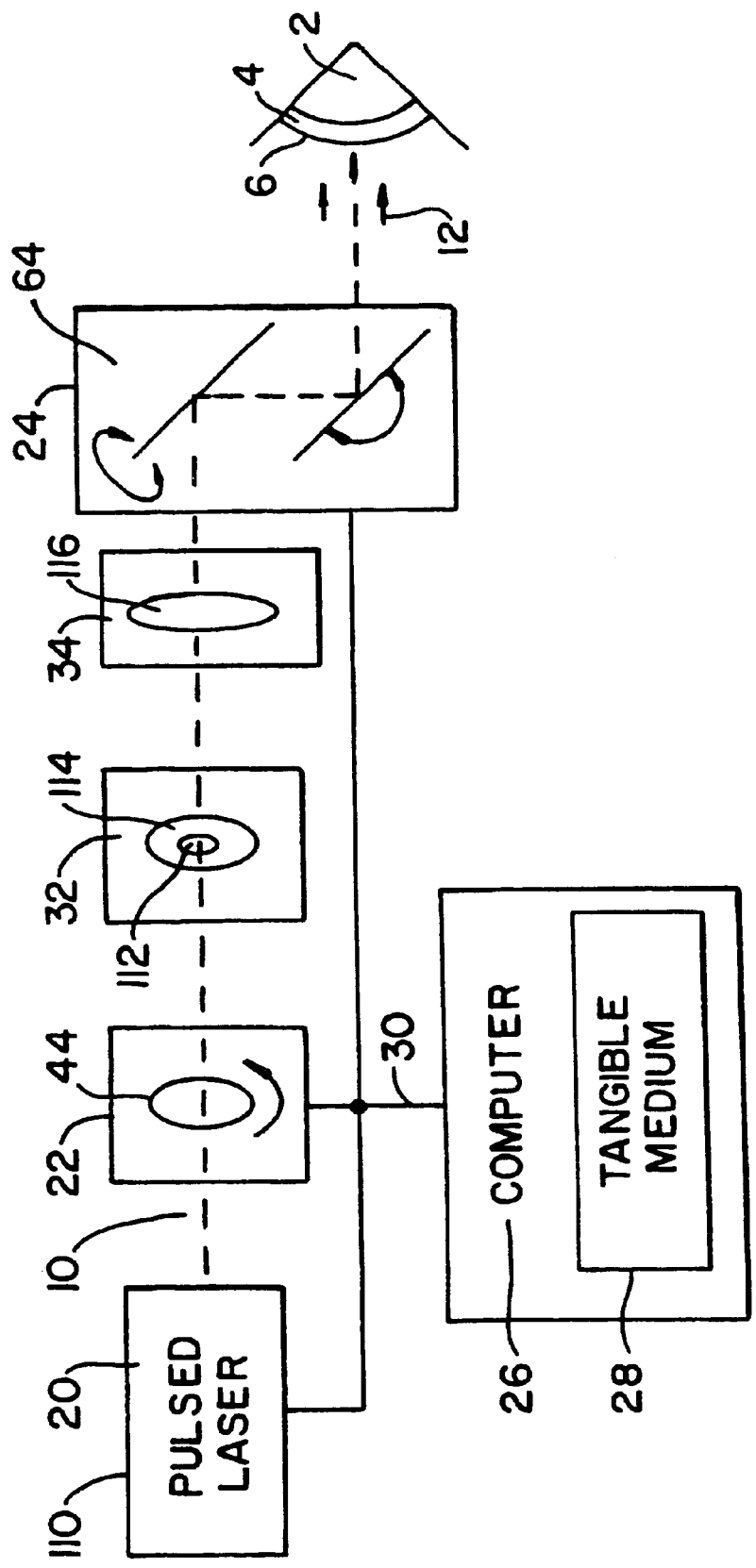
FIG. 26 illustrates an exemplary embodiment of the invention.

An exemplary embodiment of the invention is illustrated in FIG. 26. An ablative energy source 20 makes a beam of ablative energy. The ablative energy source 20 is a pulsed argon fluoride excimer laser that makes a laser beam 10 with a 193 nm output wavelength. A beam shaping element 22 is a diffractive optic that is a phase modulating transmitting element 44. The phase modulating transmitting element 44 is rotated between pulses of the laser beam 10. The shaped laser beam is restricted by beam restricting element 32. The restricting element 32 is a circular aperture 112 formed in a non-transmitting material 114 that blocks the laser beam. An imaging element 34 includes a biconvex lens 116 that forms an image of the shaped beam passing through the aperture 114 near the exposed surface 6. A laser beam scanning element 24 includes an XY mirror assembly 64. The XY mirror assembly 64 scans the consistently curved pulsed laser beam 12 over the surface 6. A computer 26 communicates with the pulsed laser 110, the rotating beam shaping element 22 and the XY mirror assembly 64. A signal connection 30 enables communication between the computer 26, the pulsed laser 110, the rotating beam shaping element 44 and the beam scanning element 24. The signal connection is preferably an opto-electronic connection such as a fiber optic connection but may be an electronic connection. The computer 26 calculates a laser treatment table including the XY coordinates of the laser beam pulses and the number of laser beam pulses at each coordinate. A person of ordinary skill in the art can calculate the positions and number of laser beam pulses at each position to produce a desired ablation shape. Other items that may be included with the invention such as an operating microscope and eye tracker have been omitted from FIG. 26 to avoid prolixity.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of sculpting a region on a surface of a tissue with a pulsed energy beam to effect a predetermined change in overall shape, the method comprising:

directing a pulsed beam of an ablative energy toward the tissue surface;

ablating a plurality of craters in the pulsed beam, wherein each pulse of the beam ablates a single associated crater having an associated crater surface extending distribution profile adjacent the tissue surface so that the associated crater surface has a consistent curvature and ablating the associated shape from a flat surface would provide a negative optical power over most of the associated crater surface; and scanning the beam over the region to effect the predetermined change in overall shape in the region by partially overlapping the plurality of consistently curved craters.

2. The method of claim 1 wherein the ablating step is performed so that a dimension across each crater is about 5 to 80% of a dimension across the region.

3. The method of claim 2 wherein the ablating step is performed so that the consistent curvature of the crater is substantially uniform and spherical, and the dimension across the craters is substantially uniform.

4. The method of claim 1 wherein the beam is a laser beam, the method further comprising shaping the energy distribution profile of the laser beam with a beam shaping element.

5. The method of claim 4 wherein the shaping step further comprises diffracting the laser beam with a diffracting element.

6. The method of claim 5 wherein the diffracting step further comprises changing an amplitude of the beam with the diffracting element.

7. The method of claim 6 wherein the diffracting step further comprises changing a phase of the beam with the diffracting element.

8. The method of claim 7 wherein the diffracting step further comprises transmitting the beam through the diffracting element to form the shaped beam with a portion of the beam passing through the element.

9. The method of claim 7 wherein the diffracting step further comprises reflecting the beam off a surface of the diffracting element to form the shaped beam with a portion of the beam reflected off the element.

10. The method of claim 4 wherein the shaping step further comprises reflecting the beam with an angle varying reflecting element.

11. The method of claim 4 wherein the shaping step further comprises refracting the beam with an angle varying refracting element.

12. The method of claim 4 wherein the shaping step further comprises transmitting the beam through a material that variably transmits the laser beam.

13. The method of claim 4 wherein the shaping step further comprises reflecting the beam off a surface that variably reflects the laser beam.

14. The method of claim 4 further comprising deflecting the beam with an optical element selected from the group consisting of lenses, prisms and mirrors.

15. The method of claim 4 further comprising restricting a cross sectional area of the beam by transmitting the beam through an aperture formed of a non-transmitting material that blocks a portion of the beam.

16. The method of claim 15 further comprising forming an image of the restricted beam near the region.

17. The method of claim 4 further comprising rotating the laser beam shaping element between pulses of the laser beam.

18. The method of claim 1 wherein together the craters increase the overall optical power of the region.

19. A laser system for sculpting an ablated region on a surface of a tissue, the tissue having a threshold of ablation, the system comprising:
   a laser for making a pulsed beam of a ablative laser energy;
   a beam energy shaping element disposed in a path of the pulsed beam, the shaping element changing a laser beam energy pattern of the pulsed beam to a shaped beam, the shaped beam comprising a consistently curved laser beam energy distribution pattern above the threshold of ablation, the energy pattern creating a consistently curved crater depth profile on the surface of the tissue with each pulse, a majority of the crater depth profile having a concave surface; and,
   a scanning element for moving the shaped beam over the region to sculpt the region with a plurality of partially overlapping pulses of the ablative energy.

20. The laser system of claim 19 wherein the consistently curved beam pattern is a substantially spherical pattern.

21. The laser system of claim 19 wherein the consistently curved beam pattern is an aspheric pattern.

22. The laser system of claim 19 wherein a central portion of the consistently curved beam pattern has a higher intensity than a spherical pattern.

23. The laser system of claim 19 wherein the scanning element comprises an optical element selected from the group consisting of lenses, prisms and mirrors.

24. The laser system of claim 19 wherein the beam shaping element comprises an element selected from the group consisting of phase modulating transmitting diffractive optics, amplitude modulating transmitting diffractive optics, phase modulating reflecting diffractive optics, amplitude modulating reflecting diffractive optics, lenses, prisms, aspheric optics, mirrors, intensity grading transmitting optics and intensity grading reflecting optics.

25. The laser system of claim 19 wherein the beam shaping element comprises a partially absorbing material.

26. The laser system of claim 19 wherein the shaped beam further comprises a boundary enclosing the consistently curved pattern, an intensity of the beam adjacent the boundary is in a range from about 100 to about 150% of the threshold of ablation.

27. The laser system of claim 26 wherein the intensity of the beam adjacent the boundary is less than about 125% of the threshold of ablation.

28. The laser system of claim 27 wherein the intensity of the beam adjacent the boundary is less than about 110% of the threshold of ablation.

29. The laser system of claim 19 further comprising a computer coupled to the scanning element so as to control a position of the beam over the region according to a coordinate reference stored in the computer.

30. The laser system of claim 29 wherein the coordinate reference partially overlaps the consistently curved pattern among the pulses of the plurality.

31. The laser system of claim 19 further comprising an aperture formed in a non-transmitting material for restricting a cross sectional area of the beam by passing the beam through the aperture.

32. The laser system of claim 31 further comprising an imaging lens for forming an image of the beam passing through the aperture, the image being formed near the ablated region.

33. A method of sculpting a region on a tissue surface with a pulsed laser beam to shape the region to a predetermined shape, the method comprising:
   making a pulsed beam of an ablative energy;
   shaping the laser beam with a beam shaping element by diffracting the laser beam with a diffracting element and changing a phase of the beam with the diffracting element by transmitting the beam through the diffracting element to form the shaped beam with a portion of the beam passing through the element;
   restricting a cross sectional area of the beam;
   forming an image of the restricted beam near the region;
   ablating a crater having a substantially uniform curvature in the tissue with a single pulse of the beam wherein the substantially uniform curvature comprises a crater shape having a negative optical power with a substantially constant magnitude, a dimension across the crater being about 5 to 80% of a dimension across the region;
   deflecting the beam;
   rotating the laser beam shaping element between pulses of the laser beam; and,
   scanning the beam over the region to form the shape in the region by partially overlapping a sequence of uniformly curved craters, the sequence of craters being distributed over the region to cover a dimension across the region and the dimension across the craters being substantially uniform among the craters of the sequence.

34. The method of claim 33 wherein together the craters increase the overall optical power of the region.

35. A method of sculpting an ablated region on an exposed corneal surface with a pulsed energy beam to shape the region to a predetermined shape, the method comprising:
   making a pulsed beam of an ablative energy, each pulse of the beam having an energy distribution profile at the corneal surface;
   ablating a crater in the corneal surface with a single pulse of the beam, wherein the crater has a crater surface extending along the corneal surface which reflects the energy distribution profile, and wherein the crater has a consistent curvature comprising a concave shape over the majority of the crater surface when ablated in a flat surface; and,
   scanning the beam over the region to form the predetermined shape in the region by partially overlapping a plurality of the consistently curved craters, the plurality of craters being distributed over the region to cover a dimension across the region.

36. The method of claim 19 wherein together the craters increase the overall optical power of the region.

37. A method of sculpting an ablated region on an exposed corneal surface with a pulsed laser beam to shape the region to a predetermined curved shape, the method comprising:
   making a pulsed beam of an ablative energy, the beam having an energy distribution profile;
   shaping the laser beam with a beam shaping element by diffracting the laser beam with a diffracting element and changing a phase of the beam with the diffracting element by transmitting the beam through the diffracting element to form the shaped beam with a portion of the beam passing through the element;
   restricting a cross sectional area of the beam by transmitting the beam through an aperture formed in a non-transmitting material that blocks a portion of the beam;

forming an image of the restricted beam near the region;

ablating a crater having a substantially uniform curvature in the tissue with a single pulse of the beam, wherein the substantially uniform curvature comprises a negative optical power with a substantially constant magnitude, a dimension across the crater being about 5 to 80% of a dimension across the region;

deflecting the beam with an optical element selected from the group consisting of lenses, prisms and mirrors;

rotating the laser beam shaping element between pulses of the laser beam to average the shaped beam; and, scanning the beam over the region to form the shape in the region by partially overlapping a sequence of uniformly curved craters, the plurality of craters being distributed over the region to cover a dimension across the region and the dimension across the craters being substantially uniform among the craters of the sequence.

38. The method of claim 20 wherein together the craters increase the overall optical power of the region.

39. A laser system for sculpting an ablated region on an exposed surface of a cornea to a predetermined curved shape, the cornea having a threshold of ablation, the system comprising:

a pulsed laser for making a pulsed beam of an ablative laser energy;

a laser beam shaping element for changing a laser beam energy pattern of the pulsed beam to a shaped beam, the shaped beam comprising a substantially spherical laser beam energy distribution pattern with a region of the substantially spherical pattern above the threshold of ablation so as to create a consistently curved crater having a crater shape with a consistent radius of curvature providing negative optical power over substantially the ablated crater surface;

a boundary enclosing the above threshold region and an intensity of the beam around the boundary being a proportion of the threshold of ablation, the proportion being in a range of 100 to 110%;

an aperture formed in a non-transmitting material for restricting a cross sectional area of the beam by passing the beam through the aperture;

an imaging lens for forming an image of the beam passing through the aperture, the image being formed near the ablated region;

a scanning element for moving the shaped beam over the region to sculpt the region to the shape with a sequence of partially overlapping pulses of the ablative energy wherein the scanning element comprises an optical element selected from the group consisting of lenses prisms and mirrors; and, a computer for controlling a position of the beam over the region according to a coordinate reference stored in the computer, the coordinate reference partially overlapping the consistently curved pattern among the pulses of the sequence.

40. A method of sculpting a region an a surface of a tissue with a pulsed energy beam to effect a predetermined change in overall shape, the method comprising:

directing a pulsed laser beam toward the tissue surface;

shaping the pulsed laser beam with a diffracting element to create an energy distribution profile, wherein each pulse of the beam ablates a single associated crater having an associated crater surface extending along the tissue surface and an associated crater shape, each pulse having the energy distribution profile adjacent the tissue surface so that the associated crater surface has a consistent curvature and ablating the associated shape from a flat surface would provide a negative optical power over most of the associated crater surface, ablating a plurality of consisting curved craters in the tissue with the energy distribution profile of pulsed beam; and scanning the beam over the region to effect the predetermined change in overall shape in the region by partially overlapping the plurality of consistently curved craters.

41. The method of claim 40, wherein the shaping step further comprises changing an amplitude of the beam with the diffracting element.

42. The method of claim 41, wherein the shaping step further comprises changing a phase of the beam with the diffracting element.

43. A laser system for sculpting an ablated region on a surface of a tissue, the tissue having a threshold of ablation, the system comprising:

a laser for making a pulsed beam of an ablative laser energy;

a diffractive optical element disposed in a path of the pulsed beam, the element changing a laser beam energy pattern of the pulsed beam to a shaped beam, the shaped beam comprising a consistently curved laser beam energy distribution pattern above the threshold of ablation, the energy pattern creating a consistently curved crater depth profile on the surface of the tissue with each pulse, a majority of the crater depth profile having a concave surface; and, a scanning element for moving the shaped beam over the region to sculpt the region with a plurality of partially overlapping pulses of the ablative energy.

44. The system of claim 43, wherein the diffracting optical element changes a phase of the beam.

45. The system of claim 43, wherein the diffracting optical element changes an amplitude of the beam.

46. The system of claim 45 or 44, wherein the diffracting optical element is configured to transmit the beam through the diffracting element to form the shaped beam with a portion of the beam passing through the element.

47. The system of claim 45 or 44, wherein the diffracting optical element is configured to reflect the beam off a surface of the diffracting element to form the shaped beam with a portion of the beam reflected off the element.

* * * * *